US011446875B2

(12) United States Patent  
Rakshit

(10) Patent No.: US 11,446,875 B2  
(45) Date of Patent: Sep. 20, 2022

(54) DEVISING A SELF-MOVEMENT PATH FOR AT LEAST ONE PRINTING DEVICE

(71) Applicant: International Business Machines Corporation, Armonk, NY (US)

(72) Inventor: Sarbajit K. Rakshit, Kolkata (IN)

(73) Assignee: International Business Machines Corporation, Armonk, NY (US)

(*) Notice: Subject to any disclaimer, the term of this patent is extended or adjusted under 35 U.S.C. 154(b) by 369 days.

(21) Appl. No.: 16/813,217

(22) Filed: Mar. 9, 2020

(65) Prior Publication Data

US 2021/0276269 A1 Sep. 9, 2021

(51) Int. Cl.
*G06F 19/00* (2018.01)
*B29C 64/386* (2017.01)
(Continued)

(52) U.S. Cl.
CPC .......... *B29C 64/386* (2017.08); *B29C 64/106* (2017.08); *B29C 64/393* (2017.08);
(Continued)

(58) Field of Classification Search
CPC ... B29C 64/393; B29C 64/106; B29C 64/386; B33Y 30/00; B33Y 50/02; G06N 20/00; C22C 30/00; B25J 9/1633; G16H 30/20
See application file for complete search history.

(56) References Cited

U.S. PATENT DOCUMENTS

2017/0100214 A1* 4/2017 Wen .................. G16H 30/20
2017/0100898 A1 4/2017 Cofler et al.
(Continued)

FOREIGN PATENT DOCUMENTS

CN 106163771 A 11/2016
CN 109807887 * 1/2019
(Continued)

OTHER PUBLICATIONS

Martel, Alexandre. The 4 Types of FHH / FDM 3D Printer Explained (Cartesian, Delta, Polar). 3Dnatives, Dec. 15, 2017. [3 printed pages] <https://www.3dnatives.com/en/four-types-fdm-3d-printers140620174/>.

(Continued)

*Primary Examiner* — Tuan A Vu  
(74) *Attorney, Agent, or Firm* — The Steadman Law Firm PLLC

(57) ABSTRACT

Techniques are described with respect to devising a self-movement path for at least one printing device. An associated method includes aggregating environmental datapoints related to at least one environmental parameter associated with a defined printing vicinity of at least one printing device and aggregating printing device datapoints related to at least one printing hardware parameter associated with the at least one printing device. The method further includes, based upon the aggregated environmental datapoints and the aggregated printing device datapoints, configuring a machine learning knowledge model to determine a self-movement path for each of the at least one printing device between a source location of the printing device and a target location of the printing device. The method further includes facilitating creation of the self-movement path for each of the at least one printing device to facilitate processing of an object within the defined printing vicinity.

20 Claims, 7 Drawing Sheets

(51) Int. Cl.
  *B29C 64/393*   (2017.01)
  *G06N 20/00*    (2019.01)
  *B29C 64/106*   (2017.01)
  *B33Y 50/02*    (2015.01)
  *B33Y 30/00*    (2015.01)
  *C22C 30/00*    (2006.01)
  *G16H 30/20*    (2018.01)
  *B25J 9/16*     (2006.01)

(52) U.S. Cl.
  CPC ............ *G06N 20/00* (2019.01); *B25J 9/1633* (2013.01); *B33Y 30/00* (2014.12); *B33Y 50/02* (2014.12); *C22C 30/00* (2013.01); *G16H 30/20* (2018.01)

(56) References Cited

U.S. PATENT DOCUMENTS

| | | | |
|---|---|---|---|
| 2017/0113799 A1 | 4/2017 | Kovac et al. | |
| 2020/0086487 A1* | 3/2020 | Johnson | B25J 9/1633 |
| 2020/0257933 A1* | 8/2020 | Steingrimsson | C22C 30/00 |

FOREIGN PATENT DOCUMENTS

| | | | |
|---|---|---|---|
| CN | 208664408 U | | 3/2019 |
| CN | 110726756 | * | 1/2020 |

OTHER PUBLICATIONS

Obudho, Brian. 3D Printer Axis: The Basics—Simply Explained. All3DP, Jul. 25, 2018. [14 printed pages] <https://all3dp.eom/2/3d-printer-axis-all-you-need-to-know/>.

* cited by examiner

DEVISING A SELF-MOVEMENT PATH FOR AT LEAST ONE PRINTING DEVICE

BACKGROUND

The various embodiments described herein generally relate to facilitating printing of an object within a defined printing vicinity. More specifically, the various embodiments describe techniques of devising a self-movement path for at least one printing device via a machine learning knowledge model.

Three-dimensional printing may facilitate creation or modification of objects or portions of objects. However, a printing device may be unable to effectively complete a printing task in a certain area consequent to a lack of functionality due to physical obstruction(s) and/or a lack of a stable path for movement. Such issues may be particularly relevant in disaster zones and/or in areas having dense vegetation or substantial structural development.

SUMMARY

The various embodiments described herein provide techniques of devising a self-movement path for at least one printing device. According to an embodiment, an associated computer-implemented method includes aggregating environmental datapoints related to at least one environmental parameter associated with a defined printing vicinity of at least one printing device and aggregating printing device datapoints related to at least one printing hardware parameter associated with the at least one printing device. The method further includes, based upon the aggregated environmental datapoints and the aggregated printing device datapoints, configuring a machine learning knowledge model to determine a self-movement path for each of the at least one printing device between a source location of the printing device and a target location of the printing device. The method further includes facilitating creation of the self-movement path for each of the at least one printing device to facilitate processing of an object within the defined printing vicinity. In an embodiment, the step of aggregating the environmental datapoints includes collecting data from a plurality of environmental sensors within the defined printing vicinity. In an additional embodiment, the step of aggregating the printing device datapoints includes collecting data from a plurality of printing device sensors associated with each of the at least one printing device.

In an embodiment, one or more of the at least one printing device include four-dimensional printing capabilities to address or enable self-movement path modification over time. In a further embodiment, the self-movement path created for a certain printing device among the at least one printing device corresponds to a footprint of the processed object. Alternatively, the self-movement path created for a certain printing device among the at least one printing device is separate from a footprint of the processed object.

In an embodiment, the step of configuring the machine learning knowledge model includes identifying a plurality of segment options for the self-movement path based upon the aggregated environmental datapoints and the aggregated printing device datapoints and training the machine learning knowledge model based upon each of the identified plurality of segment options. According to such embodiment, the step of configuring the machine learning knowledge model further includes applying at least one artificial intelligence algorithm to select a segment option among the identified plurality of segment options to add to the self-movement path. Optionally, each selected segment option is determined at a defined point in time based upon the aggregated environmental datapoints and the aggregated printing device datapoints identified prior to the defined point in time. Furthermore, according to such embodiment, the step of configuring the machine learning knowledge model includes updating the machine learning knowledge model based upon the selected segment option among the identified plurality of segment options.

In an embodiment, the step of facilitating creation of the self-movement path for each of the at least one printing device includes devising at least one shape of the self-movement path based upon at least one predefined shape factor selected from the group consisting of shape of the processed object, degree of complexity of the processed object, available print space, print frequency, printing device quantity, and printing device physical attributes. The step of facilitating creation of the self-movement path for each of the at least one printing device further includes, responsive to determining that a preexisting self-movement path between the source location and the target location is available for the printing device, incorporating at least one segment of the preexisting self-movement path into the self-movement path. The step of facilitating creation of the self-movement path for each of the at least one printing device further includes, responsive to determining that no preexisting self-movement path between the source location and the target location is available for the printing device, devising an entirely new route for the self-movement path.

One or more additional embodiments pertain to a computer program product including a computer readable storage medium having program instructions embodied therewith. According to such embodiment(s), the program instructions may be executable by a computing device to cause the computing device to perform one or more steps of above recited computer-implemented method. One or more further embodiments pertain to a system having a processor and a memory storing an application program, which, when executed on the processor, performs one or more steps of the above recited computer-implemented method.

BRIEF DESCRIPTION OF THE DRAWINGS

So that the manner in which the above recited aspects are attained and can be understood in detail, a more particular description of embodiments, briefly summarized above, may be had by reference to the appended drawings.

Note, however, that the appended drawings illustrate only typical embodiments of this invention and are therefore not to be considered limiting of its scope, for the invention may admit to other equally effective embodiments.

DETAILED DESCRIPTION

Figure 1:
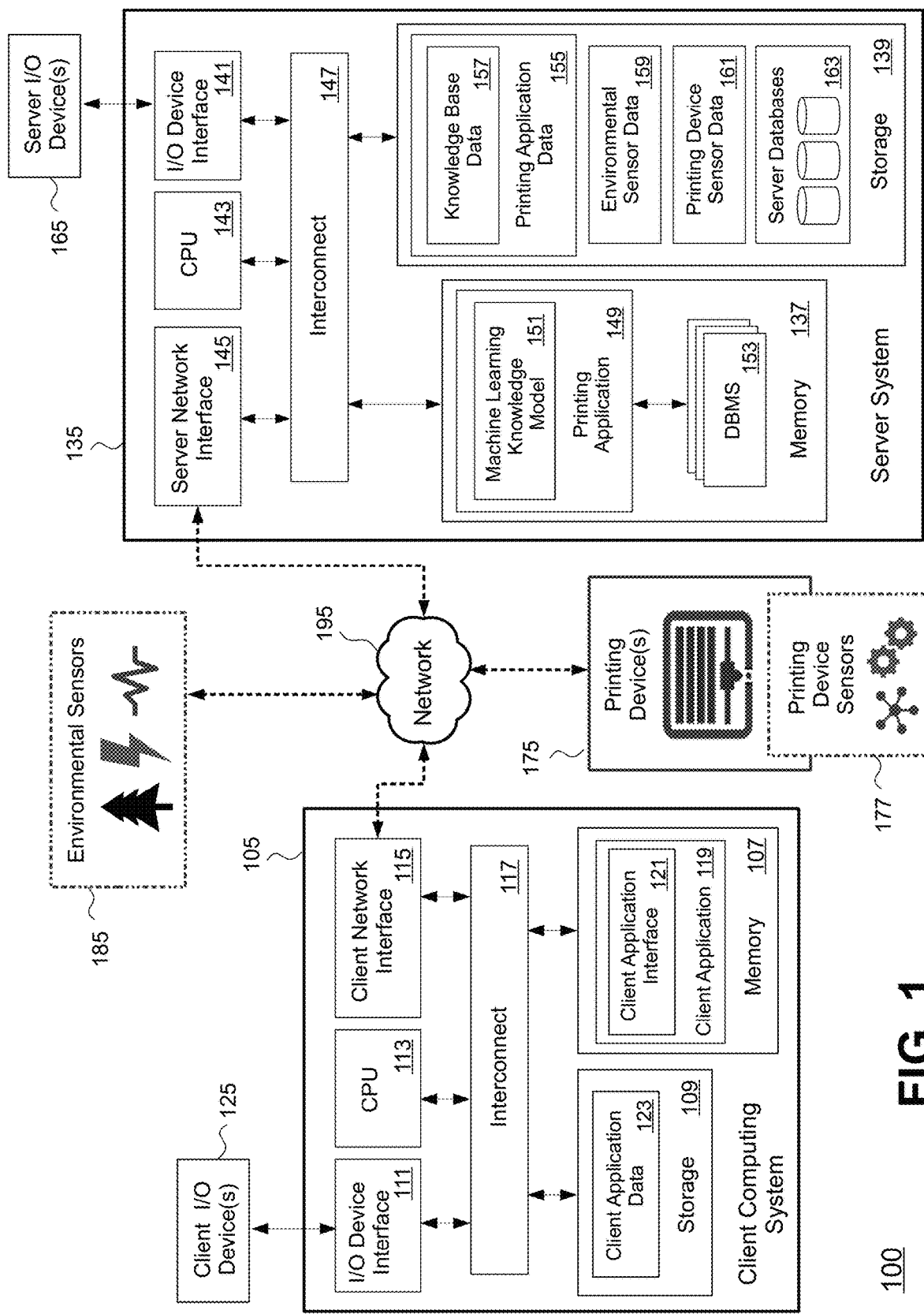
FIG. 1 illustrates a computing infrastructure, according to one or more embodiments.

The various embodiments described herein are directed to techniques of devising a self-movement path for at least one printing device. A printing application configured to implement techniques associated with the various embodiments described herein configures a machine learning knowledge model to determine a self-movement path for each of at least one printing device based upon aggregated environmental datapoints and aggregated printing device datapoints. A determined self-movement path optionally corresponds to a footprint of an object processed in the context of a three-dimensional printing task, or alternatively such determined self-movement path is created separately from such footprint.

The various embodiments described herein may have advantages over conventional techniques. Specifically, the various embodiments may improve computer technology by utilizing machine learning to determine and facilitate creation of a self-movement path for at least one printing device within a defined printing vicinity. Accordingly, the at least one printing device may access an area within the defined printing vicinity via the created self-movement path in order to process an object, which may entail creating such object via printing and/or modifying such object via printing, repairing, and/or otherwise enhancing. The created self-movement path optionally provides a physically defined and/or electronically defined track for the at least one printing device and optionally accommodates at least one supporting entity to which the at least one printing device is mounted or connected, such as a mobile device platform or a drone. Some of the various embodiments may not include all such advantages, and such advantages are not necessarily required of all embodiments.

In the following, reference is made to various embodiments of the invention. However, it should be understood that the invention is not limited to specific described embodiments. Instead, any combination of the following features and elements, whether related to different embodiments or not, is contemplated to implement and practice the invention. Furthermore, although embodiments may achieve advantages over other possible solutions and/or over the prior art, whether or not a particular advantage is achieved by a given embodiment is not limiting. Thus, the following aspects, features, embodiments, and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network, and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++, or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions also may be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions also may be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Particular embodiments describe techniques relating to devising a self-movement path for at least one printing device. However, it is to be understood that the techniques described herein may be adapted to a variety of purposes in addition to those specifically described herein. Accordingly, references to specific embodiments are included to be illustrative and not limiting.

FIG. 1 illustrates a computing infrastructure 100, according to an embodiment. As shown, computing infrastructure 100 includes a client computing system 105, a server system 135, at least one printing device 175 having a plurality of printing device sensors 177 associated therewith, and a plurality of environmental sensors 185, each connected to a communications network 195.

Illustratively, client computing system 105 includes, or is otherwise operatively coupled to, a memory 107, storage 109, an input/output (I/O) device interface 111, a central processing unit (CPU) 113, and a client network interface 115, all of which are interconnected via interconnect 117 (e.g., a bus). Client computing system 105 optionally is or includes a smartphone, a laptop, a desktop, and/or another hardware computing device. One or more aspects of client computing system 105 are accessed or controlled by one or more clients, such as a client requesting and/or facilitating completion of a printing activity. Although shown as a single computing system, client computing system 105 is included to be representative of a single client or multiple clients. In an embodiment, client computing system 105 is a thin client. Memory 107 includes a client application 119. Client application 119 is optionally an online application configured for interfacing with server system 135 and other computing systems. Client application 119 includes a client application interface 121. In the event of multiple clients, multiple instances of client computing system 105 may be present, each having a respective client application 119 including at least one respective client application interface 121. Client application interface 121 includes a graphical user interface (GUI), a command line interface, and/or a sensory interface (e.g., capable of discerning and processing client sound/voice commands). The one or more clients may designate one or more printing preferences and otherwise may communicate with server system 135 via client application interface 121. In an embodiment, client application 119 optionally applies natural language processing (NLP), e.g., natural language processing (NLU), to process natural language command(s) provided by one or more clients. To complete a NLP-related task in the context of the various embodiments described herein, client application 119 optionally initiates or otherwise facilitates an application programming interface (API) call to an application having natural language processing capabilities, e.g., a cloud-based NLP application. In a further embodiment, client application 119 optionally applies audiovisual processing to process voice-based and/or image-based command(s) provided by one or more clients. To complete an audiovisual processing-related task in the context of the various embodiments described herein, client application 119 optionally initiates or otherwise facilitates an API call to an application having audiovisual processing capabilities, e.g., a cloud-based audiovisual processing application.

Storage 109 includes client application data 123 associated with client application 119. One or more components of a GUI, a command line interface, and/or a sensory interface included in client application interface 121 may facilitate client input and/or may facilitate display of client application data 123. I/O device interface 111 is communicatively coupled to one or more client I/O devices 125 (e.g., touchscreen console, trackpad, joystick, microphone, speaker, etc.). The client(s) may interact with client application interface(s) 121 via the one or more client I/O devices 125. CPU 113 is included to be representative of a single CPU, multiple CPUs, a single CPU having multiple processing cores, and the like. Client network interface 115 is configured to receive data from and transmit data to server system 135 via network 195.

Although shown as a single computing system, server system 135 is included to be representative of a single server system or multiple server systems. In an embodiment, server system 135 includes a single hardware server configured to provide hosting capabilities. In an alternative embodiment, server system 135 includes, or is otherwise operatively coupled to, a plurality of hardware and/or virtualized servers configured to provide hosting capabilities. In a further alternative embodiment, server system 135 is a cloud server system configured to provide distributed hosting capabilities via a plurality of cloud computing nodes in a cloud computing environment. According to such further alternative embodiment, the cloud computing nodes are configured to communicate with one another. Additionally, according to such further alternative embodiment, the cloud computing environment optionally offers infrastructure, platforms, and/or software as a service for which client computing system 105 or other systems associated with computing infrastructure 100 need not maintain resources locally.

Illustratively, server system 135 includes, or is otherwise operatively coupled to, memory 137, storage 139, an I/O device interface 141, a CPU 143, and a server network interface 145, all of which may be interconnected via interconnect 147 (e.g., a bus). Memory 137 includes a printing application 149. Printing application 149 includes or is otherwise operatively coupled to a machine learning knowledge model representation 151. In an embodiment, printing application 149 is configured to execute one or more artificial intelligence algorithms utilizing one or more machine learning techniques via machine learning knowledge model representation 151. According to such embodiment, machine learning knowledge model representation 151 includes or is otherwise operatively coupled to a machine learning knowledge model and at least one knowledge base associated therewith. According to such embodiment, some or all aspects of the machine learning knowledge model may run within server system 135. Additionally or alternatively, some or all aspects of machine learning knowledge model may run externally to server system 135, e.g., via a cloud-based implementation, in which case server system 135 communicates with the machine learning knowledge model via machine learning knowledge model representation 151. Some or all aspects of the at least one knowledge base optionally are incorporated into server system 135. Alternatively, some or all aspects of the at least one knowledge base are externally located and communicatively coupled to server system 135.

Memory 137 further includes or is otherwise operatively coupled to database management system (DBMS) 153. DBMS 153 is included to be representative of a single database system or multiple database systems. Printing application 149 is configured to devise a self-movement path for one or more of the at least one printing device 175 according to the various embodiments described herein. Printing application 149 further is configured to facilitating processing of an object via one or more of the at least one printing device 175. Specifically, through one or more of the at least one printing device 175, printing application 149 is configured to facilitate creation of such object via printing, and/or is configured to facilitate modification of such object via printing, repairing, and/or otherwise enhancing. In an embodiment, printing application 149 facilitates authentication of client computing system 105 and/or other client systems in computing infrastructure 100. In an alternative embodiment, printing application 149 sends authentication information associated with client computing system 105 and/or other client systems to an external directory server system, which may in turn perform any necessary authentication steps. In an alternative embodiment, some or all of the aspects of server system 135, including some or all functional capabilities of printing application 149, are incorporated into one or more of the at least one printing device 175. In a further alternative embodiment, some or all of the aspects of server system 135, including some or all functional capabilities of printing application 149, are incorporated into client computing system 105.

Storage 139 includes printing application data 155. Printing application 149 generates and processes printing application data 155 based on interaction with other components of computing infrastructure 100. Printing application data 155 includes knowledge base data 157 generated and/or used by the machine learning knowledge model. Knowledge base data 157 includes datapoints pertaining to self-movement path segment options. Printing application data 155 further includes any data associated with processing (e.g., creating or modifying) an object. In an embodiment, knowledge base data 157 includes data associated with the at least one knowledge base. Storage 139 further includes environmental sensor data 159, including aggregated environmental datapoints, associated with (e.g., received from) the plurality of environmental sensors 185. Storage 139 further includes printing device sensor data 161, including aggregated printing device datapoints, associated with (e.g., received from) the plurality of printing device sensors 177. Storage 139 further includes server databases 163. DBMS 153 includes or interfaces with a software application configured to manage server databases 163. In an embodiment, printing application 149 sends database requests to DBMS 153 and processes results returned by DBMS 153. In a further embodiment, server databases 163 include one or more relational databases. In an additional embodiment, server databases 163 include one or more ontology trees or other ontological structures. While FIG. 1 shows three server databases 163 for illustrative purposes, server system 135 (and more generally computing infrastructure 100) may include any number of databases. According to a further embodiment, DBMS 153 sends requests to remote databases (not shown) via network 195.

I/O device interface 141 is communicatively coupled to one or more server I/O devices 165. CPU 143 is included to be representative of a single CPU, multiple CPUs, a single CPU having multiple processing cores, and the like. Server network interface 145 is configured to receive data from and transmit data to client computing system 105 or other client system(s) via network 195. Specifically, printing application 149 is configured to accept request(s) sent by client computing system 105 or other client system(s) to server system 135 and is configured to transmit data to client computing system 105 or other client system(s) via server network interface 145. Furthermore, server network interface 145 is configured to receive data from and/or transmit data to the at least one printing device 175, the plurality of printing device sensors 177, and/or the plurality of environmental sensors 185 via network 195.

The at least one printing device 175 is configured to process an object, e.g., a two-dimensional structure or a three-dimensional structure, based upon input received from server system 135, more specifically printing application 149. Each of the at least one printing device is configured to process an object by creating the object via printing and/or by modifying the object via printing, repairing, and/or otherwise enhancing. As further described herein with respect to FIG. 2, a dice attached to, incorporated into, or otherwise associated with a printing device among the at least one printing device 175 is configured to create a self-movement path by printing such self-movement path (e.g., creating a physical representation) or otherwise marking such self-movement path (e.g., designating an electronic representation). In an embodiment, one or more of the at least one printing device 175 is a two-dimensional printer, a three-dimensional printer, or other hardware device configured to process an object. Additionally, one or more of the at least one printing device 175 includes structural enhancement components that provide capabilities in addition to printing. Such structural enhancement components optionally include hardware tools and/or hardware portions configured to repair or otherwise enhance an object. An example printing device among the at least one printing device 175 is described in further detail with respect to FIG. 2.

The plurality of printing device sensors 177 are Internet of Things (IoT) sensors capable of communicating with other systems or devices in computing infrastructure 100, including client computing system 105, server system 135, the at least one printing device 175, and/or the plurality of environmental sensors 185. In an embodiment, the plurality of printing device sensors 177 include analog sensors and/or digital sensors. One or more sensors among the plurality of printing device sensors 177 optionally include both analog characteristics and digital characteristics. One or more of the plurality of printing device sensors 177 are located on, attached to, integrated into, or otherwise associated with one or more of the at least one printing device 175 and/or at least one supporting entity of one or more of the at least one printing device 175. At least one supporting entity optionally includes a drone to which a printing device among the at least one printing device 175 is attached or otherwise linked. Additionally or alternatively, at least one supporting entity optionally includes a mobile device platform on which or to which a printing device among the at least one printing device 175 is mounted or otherwise positioned. In an embodiment, the plurality of printing device sensors 177 include photographic sensors and/or video sensors (e.g., within a photographic camera or a video camera) configured to capture photographic imagery and/or video imagery. In a further embodiment, the plurality of printing device sensors 177 include audio sensors (e.g., within a microphone) configured to capture audio.

The plurality of environmental sensors 185 are IoT sensors capable of communicating with other systems or devices in computing infrastructure 100, including client computing system 105, server system 135, the at least one printing device 175, and/or the plurality of printing device sensors 177. In an embodiment, the plurality of environmental sensors 185 include analog sensors and/or digital sensors. One or more sensors among the plurality of environmental sensors 185 optionally include both analog and digital characteristics. In an embodiment, the plurality of environmental sensors 185 include photographic sensors and/or video sensors (e.g., within a photographic camera or a video camera) configured to capture photographic imagery and/or video imagery. In a further embodiment, the plurality of environmental sensors 185 include audio sensors (e.g., within a microphone) configured to capture audio.

One or more aspects of computing infrastructure 100, including client application 119 of client computing system 105, printing application 149 of server system 135, the at least one printing device 175, plurality of printing device sensors 177, and/or the plurality of environmental sensors 185 are configured to provide appropriate client notice with respect to any personal data collection associated with printing commands/preferences or other aspects. One or more aspects of computing infrastructure 100 further are configured to provide a client an option to opt in or opt out of any such personal data collection at any time. Optionally, one or more aspects of computing infrastructure 100 further are configured to transmit at least one notification to any affected client each time any such personal data collection occurs.

Figure 2:
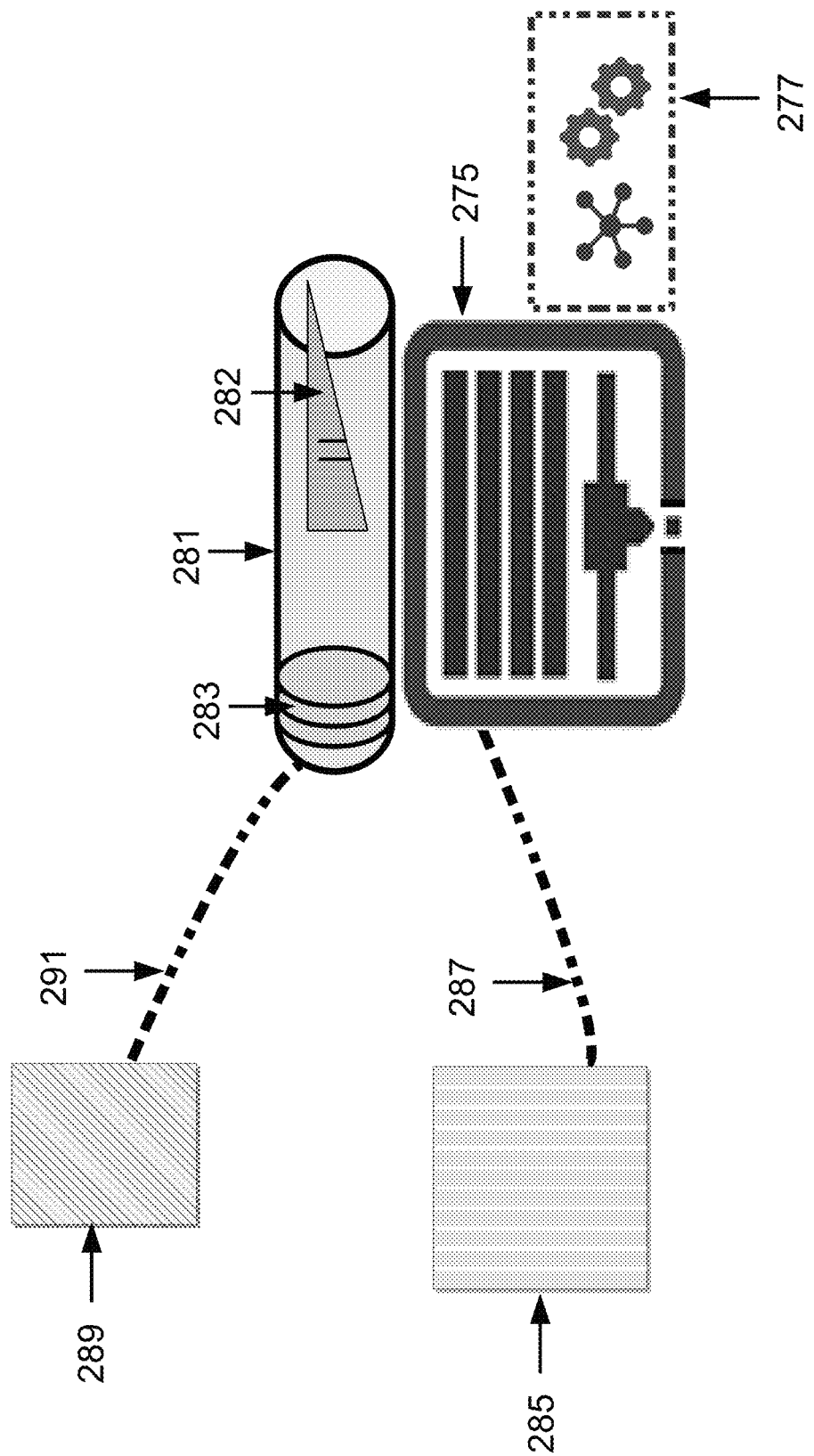
FIG. 2 illustrates an example printing device and related components.

FIG. 2 illustrates an example printing device 275 and related components. Printing device 275 optionally is among the at least one printing device 175 in computing infrastructure 100. Printing device 275 is associated with a plurality of printing device sensors 277. The plurality of printing device sensors 277 optionally are among the plurality of printing device sensors 177 in computing infrastructure 100. A dice 281 is attached to or otherwise associated with printing device 275. In the context of the various embodiments described herein, a dice is a physical structure configured to facilitate creation of a self-movement path for a printing device. In the context of computing infrastructure 100, the printing application 149 optionally facilitates deposition of printing material to mark and/or create a supporting structure for a self-movement path within the defined printing vicinity via a dice, e.g., dice 281. Dice 281 includes a cutting element 282 configured to physically reduce or eliminate any physical obstruction within a determined self-movement path (and optionally within a defined buffer zone of the determined self-movement path) and/or configured to establish a physical foundation for a determined self-movement path. Optionally, cutting element 282 is a physical cutting blade or multiple physical cutting blades. Alternatively, cutting element 282 is a hardware apparatus including at least one blade (e.g., at least one metal blade). Optionally, cutting element 282 incorporates an electric current to facilitate a mechanical cutting via at least one element (e.g., at least one blade) thereof. Optionally, cutting element 282 is retractable such that it is visible and/or ready for use only when a cutting activity is required on the part of dice 281. Furthermore, during the process of creating a determined self-movement path, optionally dice 281 is configured to store and deposit printing material in printing material compartments 283. While shown as multiple compartments, alternatively dice 281 includes a single printing material compartment.

A printing material reservoir 285, such as a tank or other durable container, is configured to provide printing material to printing device 275. A connection segment 287, comprised of flexible pipe and/or another type of conduit, is configured to relay printing material from printing material reservoir 285 to printing device 275. Printing material provided to printing device 275 optionally enables object processing, e.g., via structural printing and/or modification. A printing material reservoir 289, such as a tank or other durable container, is configured to provide printing material to dice 281. A connection segment 291, comprised of flexible pipe and/or another type of conduit, is configured to relay printing material from printing material reservoir 289 to dice 281. Printing material provided to dice 281 optionally facilitates self-movement path creation, e.g., by creating a supporting structure and/or by marking parameters of a physical or electronically defined track. As illustrated in FIG. 2, printing material reservoirs 285 and 289 separately provide printing material from separate sources to printing device 275 and dice 281 respectively. Optionally, printing material reservoirs 285 and 289 include a single printing material, in which case such single printing material both facilitates self-movement path creation via dice 281 and facilitates object processing via printing device 275 (and optionally via one or more additional printing device(s)) during a printing activity. Alternatively, printing material reservoirs 285 and 289 include different respective printing materials, in which case a first printing material facilitates self-movement path creation via dice 281 and a second printing material facilitates object processing via printing device 275 (and optionally via one or more additional printing device(s)) during a printing activity. In an alternative embodiment (not shown), a single printing material reservoir optionally routes a single printing material to both printing device 275 and dice 281. In an embodiment, dice 281 facilitates solidification of any printing material routed thereto from printing material reservoir 289 by storing such printing material for a certain duration in one or more of printing material compartments 283 prior to deposition. Such solidification facilitates self-movement path creation. For instance, solidification of a relatively dense printing material may be necessary for a self-movement path requiring relatively greater support, e.g., a path having thicker and/or vertical elements. In an alternative embodiment, dice 281 is configured to facilitate electronic marking of a determined self-movement path in lieu of or in addition to facilitating physical marking of such determined self-movement path through deposition of printing material.

Figure 3:
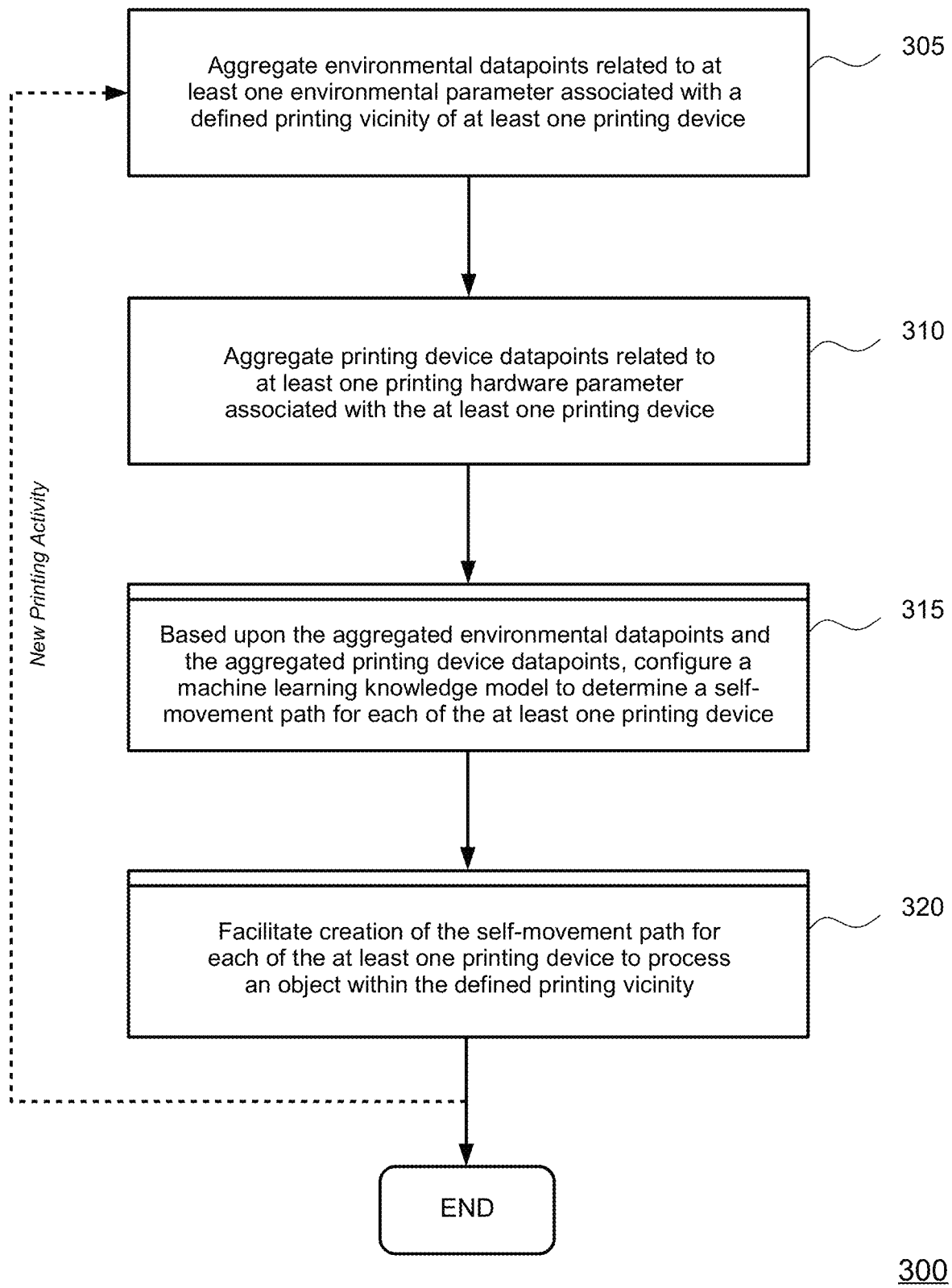
FIG. 3 illustrates a method of devising a self-movement path for each of at least one printing device, according to one or more embodiments.

FIG. 3 illustrates a method 300 of devising a self-movement path for at least one printing device (e.g., at least one printing device 175 in computing infrastructure 100, an example of which is illustrated as printing device 275 in FIG. 2). In an embodiment, one or more of the at least one printing device is a three-dimensional printer or other hardware device configured to process an object, e.g., configured to create or modify a three-dimensional object. One or more steps associated with the method 300 and the other methods described herein may be carried out in a client-server computing environment (e.g., computing infrastructure 100) including a network (e.g., network 195). A printing application in a server system of the client-server computing environment (e.g., printing application 149 in server system 135 of computing infrastructure 100) facilitates processing according to the method 300 and the other methods described herein. The printing application interacts with each of one or more clients via a respective client interface associated with a client application of a client computing system (e.g., client application interface 121 associated with client application 119 of client computing system 105). Additionally or alternatively to the client-server computing environment, one or more steps associated with the method 300 and the other methods described herein may be carried out within one or more workloads of a cloud computing environment. Additionally or alternatively, one or more steps associated with the method 300 and the other methods described herein may be carried out in a peer-to-peer network environment, in which case one or more of the method steps described herein may be carried out via a peer application of a peer computing system. Additionally or alternatively, one or more steps associated with the method 300 and the other methods described herein may be carried out directly via one or more of the at least one printing device.

The method 300 begins at step 305, where the printing application aggregates environmental datapoints related to at least one environmental parameter associated with a defined printing vicinity of the at least one printing device. In an embodiment, the printing application provides a client associated with the client computing system an option to designate the defined printing vicinity. According to such embodiment, the printing application provides an option to designate the defined printing vicinity based upon identifying locational coordinates, e.g., as marked by Global Positioning System (GPS) coordinates, as marked by radar, and/or as marked by lidar. Additionally or alternatively, the printing application provides an option to designate the defined printing vicinity based upon identifying a locational range, e.g., as marked by physical landmarks such as rocks and/or posts and/or as marked electronically and accessible via GPS, a computer network, etc. In an alternative embodiment, the printing application determines the defined printing vicinity based upon a pathway between a source location associated with a certain printing device among the at least one printing device and a target location associated with the certain printing device. According to such alternative embodiment, the printing application identifies the defined printing vicinity based upon a designated directional range, e.g., a radial distance extended in all directions or extended in a predetermined directional range, from a pathway between a source location associated with a certain printing device and a target location associated with the certain printing device. In the event that there are multiple printing devices, the printing application optionally designates the defined printing vicinity based upon a combination of designated directional ranges, e.g., respective radial distances extended in all directions or extended in respective predetermined directional ranges, from pathways between respective source locations and respective target locations associated with each of the multiple printing devices, or a subset thereof. In the context of the various embodiments described herein, a source location associated with a certain printing device among the at least one printing device is a location at which the certain printing device commences printing in the context of a printing activity. The source location for a certain printing device among the at least one printing device may coincide with the current location of the certain printing device. In the context of the various embodiments described herein, a target location associated with a certain printing device among the at least one printing device is a location at which the certain printing device concludes printing in the context of a printing activity.

In an embodiment, the printing application executes step 305 and other steps of the method 300 during a printing activity. In the context of the various embodiments described herein, a printing activity is defined as any task in the context of object processing within the defined printing vicinity within a predetermined duration. An example printing activity may entail creating and/or modifying a defined three-dimensional structure such as a modular house or an emergency shelter in an area affected by a disaster or another emergency within a one-month period. For instance, the printing application may facilitate processing of repairs to a damaged structure during a printing activity initiated in the aftermath of a fire. In another instance, the printing application may facilitate creation of a new structure during a printing activity initiated in an area affected by an earthquake.

The at least one environmental parameter optionally includes weather or climate conditions associated with the defined printing vicinity. Additionally or alternatively, the at least one environmental parameter includes geographic or locational characteristics associated with the defined printing vicinity. Additionally or alternatively, the at least one environmental parameter pertains to any physical obstruction within or otherwise associated with the defined printing vicinity. Any such physical obstruction optionally is natural, such as a tree or a river, and/or previously constructed (artificial), such as a preexisting building or a concrete dam. In an embodiment, the printing application aggregates the environmental datapoints at step 305 by collecting data from a plurality of environmental sensors (e.g., the plurality of environmental sensors 185) within the defined printing vicinity. According to such embodiment, with regard to weather or climate conditions associated with the defined printing vicinity, the collected environmental sensor data optionally includes temperature, humidity level, precipitation level, ultraviolet light level, air quality level, barometric pressure, wind speed, wind direction, etc. Furthermore, according to such embodiment, with regard to geographic or locational characteristics associated with the defined printing vicinity, the collected environmental sensor data optionally includes information pertaining to topography, seismic activity, natural resources, demographics, political boundaries, cultural attractions, restaurants, amusements, etc. Furthermore, according to such embodiment, with regard to any physical obstruction within or otherwise associated with the defined printing vicinity, the collected environmental sensor data optionally includes locational information and/or physical/structural attributes (e.g., length, width, height, weight/mass, volume, level of transparency) pertaining to any such physical obstruction. One or more of the plurality of environmental sensors optionally collect information with regard to geographic or locational characteristics and/or information with regard to any physical obstruction via Internet resources (e.g., assessed via a cloud network), radar, lidar, and/or a location detection service (e.g., GPS). In a further embodiment, at least one photographic/video sensor among the plurality of environmental sensors (e.g., among camera sensors) and/or at least one IoT sensor feed created based upon data collection from the plurality of environmental sensors optionally facilitate collection and analysis of information with regard to geographic or locational characteristics and/or information with regard to any physical obstruction.

At step 310, the printing application aggregates printing device datapoints related to at least one printing hardware parameter associated with the at least one printing device. In an embodiment, the at least one printing hardware parameter includes weight/mass metrics pertaining to one or more of the at least one printing device. In another embodiment, the at least one printing hardware parameter includes printing material selection. In a further embodiment, the at least one printing hardware parameter includes printing device distance to be travelled by one or more of the at least one printing device. In a further embodiment, the at least one printing hardware parameter includes altitude, velocity, and/or acceleration of one or more of the at least one printing device, e.g., during attachment to a drone and/or during attachment to a mobile device platform. In a further embodiment, the at least one printing hardware parameter includes external force applied to one or more of the at least one printing device, e.g., based upon temperature, wind speed, wind direction, humidity level, barometric pressure, presence of physical obstruction(s), printing device altitude, printing device velocity, printing device acceleration, etc.

In an embodiment, the printing application aggregates the printing device datapoints at step 310 by collecting data from a plurality of printing device sensors (e.g., the plurality of printing device sensors 177) associated with each of the at least one printing device. Each of the plurality of printing device sensors optionally is associated with a single printing device among the at least one printing device or alternatively is associated with multiple printing devices among the at least one printing device. The plurality of printing device sensors optionally track metrics related to the at least one printing hardware parameter. In an embodiment, at least one photographic/video sensor among the plurality of printing device sensors (e.g., among camera sensors) optionally facilitates measurement of printing device distance travelled, printing device altitude, printing device velocity, printing device acceleration, and/or other locational/inertial aspects associated with one or more of the at least one printing device within the defined printing vicinity. Additionally or alternatively, ultrasound scanning features among the plurality of printing device sensors optionally facilitate measurement of printing device distance travelled and/or other locational/inertial aspects within the defined printing vicinity. Additionally or alternatively, at least one IoT sensor feed created based upon data collection from the at least one environmental sensor and/or the at least one printing device sensor facilitates measurement of distance between two designated locations within the defined printing vicinity, printing device distance travelled, printing device altitude, printing device velocity, printing device acceleration, and/or other locational/inertial aspects within the defined printing vicinity. The printing application optionally facilitates separate aggregation of printing device datapoints with respect to a certain printing device among the at least one printing device by collecting data from printing device sensors among the plurality of printing device sensors specifically associated with the certain printing device. Additionally or alternatively, the printing application facilitates collective aggregation of printing device datapoints with respect to multiple printing devices among the at least one printing device by collating or otherwise organizing data from printing device sensors among the plurality of printing device sensors associated with the multiple printing devices. Based upon such data collation, the printing application may identify one or more comparative data trends associated with the multiple printing devices, e.g., printing device travel patterns.

At step 315, based upon the aggregated environmental datapoints and the aggregated printing device datapoints, the printing application configures a machine learning knowledge model to determine a self-movement path for each of the at least one printing device between a source location associated with the printing device and a target location associated with the printing device. According to step 315, in the event that the at least one printing device includes a single printing device, the printing application optionally determines a single self-movement path for the single printing device. Alternatively, in the event that the at least one printing device includes multiple printing devices, the printing application determines multiple respective self-movement paths for the multiple printing devices. According to such alternative, the multiple respective self-movement paths optionally include one or more common path segments shared among two or more of the multiple printing devices. In the context of the various embodiments described herein, the machine learning knowledge model is a hardware path learning model. In an embodiment, the printing application determines respective self-movement path segments including aspects that proceed laterally at ground level, e.g., aspects that are partially or entirely in contact with the ground. Additionally or alternatively, the printing application determines respective self-movement path segments including one or more aspects above ground level. The one or more aspects above ground level optionally include aspects that run vertically, aspects that run at an angle to ground level, aspects that run parallel to the ground but not in contact with the ground, and/or aspects that proceed at one or more altitudes above ground level. In an embodiment in which there are multiple printing devices, the printing application may determine respective self-movement paths, or segments thereof, for one or more of the multiple printing devices based upon environmental datapoints among the aggregated environmental datapoints and/or printing device datapoints among the aggregated printing device datapoints associated with each of the multiple printing devices, or a subset thereof. A method with regard to configuring the machine learning knowledge model in accordance with step 315 is described herein with respect to FIG. 6.

At step 320, the printing application facilitates creation of the self-movement path for each of the at least one printing device in order to facilitate processing of an object within the defined printing vicinity. In an embodiment, the printing application facilitates processing of the object by facilitating creation of the object via one or more of the at least one printing device (e.g., facilitating initial printing and/or other construction of the object). Additionally or alternatively, the printing application facilitates processing of the object by facilitating modification of the object via one or more of the at least one printing device (e.g., facilitating repair or enhancement of an already existing component of the object and/or facilitating printing of an additional component or portion of the object). In a further embodiment, the printing application facilitates processing of the object according to step 320 during a printing activity.

The self-movement path created for each printing device among the at least one printing device according to step 320 is configured to facilitate mobility and/or guidance of the printing device within the defined printing vicinity. In an embodiment, a self-movement path created for a certain printing device among the at least one printing device is reverse traversable. A reverse-traversable self-movement path may enable the certain printing device to return to the source location associated with the certain printing device (or other self-movement path location(s)) upon reaching the target location associated with the certain printing device and/or may enable the certain printing device to return to the source location (or other self-movement path location(s)) during a printing activity, e.g. in the event of an emergency or upon client request. According to such embodiment, optionally multiple respective self-movement paths created for multiple printing devices among the at least one printing device are reverse traversable. In an additional embodiment, a self-movement path created for a certain printing device among the at least one printing device accommodates at least one supporting entity of the certain printing device. The at least one supporting entity is configured to facilitate mobility and/or guidance along the self-movement path created for the certain printing device (e.g., along a track marked or otherwise delineated) and/or is configured to provide access and/or stability for object processing. Each of the at least one supporting entity comprises a physical structure configured to fully or partially sustain the certain printing device or portion(s) thereof. According to such additional embodiment, the at least one supporting entity includes a drone. Additionally or alternatively, the at least one supporting entity includes a mobile device platform. According to such additional embodiment, optionally multiple respective self-movement paths created for multiple printing devices among the at least one printing device accommodate respective supporting entities.

In an embodiment, the printing application facilitates creation of the self-movement path for each printing device among the at least one printing device through deposition of printing material, through deposition of physical marker(s) such as light(s) or post(s), and/or through deposition or designation of electronic markers. According to such embodiment, the self-movement path created for a certain printing device among the at least one printing device optionally is marked or otherwise delineated by a track. According to such embodiment, the track may be a physical lane via which the printing application facilitates mobility and/or guidance of the certain printing device. Optionally the physical lane is created dynamically by a dice associated with the certain printing device (e.g., dice 281), for instance through deposition of printing material relayed to the dice from at least one printing reservoir (e.g., printing reservoir 289). Optionally, any mobile device platform on which the certain printing device is mounted is connected or otherwise associated with the physical lane, in which case the printing application facilitates mobility and/or guidance of any such mobile device platform along the track, e.g., via a wheel or a set of wheels, via a gear rack, via a string or rope, and/or via a locking mechanism. Additionally or alternatively, the track may be defined electronically, e.g., via light beams. Optionally the certain printing device is attached to or otherwise connected to a drone or another device facilitating movement thereof, in which case the printing application may facilitate mobility and/or guidance of the drone/other device via the electronically defined track. According to such embodiment, optionally each of multiple respective self-movement paths created for multiple printing devices among the at least one printing device is marked or otherwise delineated by a physically defined track and/or an electronically defined track. In a further embodiment, the self-movement path created for a certain printing device among the at least one printing device optionally is traversable by one or more other printing devices. According to such further embodiment, the self-movement path optionally includes one or more common path segments. According to such further embodiment, in the event that the self-movement path is marked or otherwise delineated by a track, the printing application optionally facilitates mobility and/or guidance of multiple printing devices among the at least one printing device via the track or segment(s) thereof.

In an embodiment, one or more printing devices among the at least one printing device include four-dimensional printing capabilities, specifically to enable self-movement path modification over time and/or to address future issues resulting from a created self-movement path. The fourth dimension in the context of four-dimensional printing generally pertains to transformation over time. In the context of the various embodiments described herein, the fourth dimension pertains to transformation over time of self-movement path(s) created in accordance with step 320. The printing application optionally applies four-dimensional printing capabilities to account for self-movement path modification over time (e.g., path decay based upon environmental factors such as weather or climate, etc.). Additionally or alternatively, if a created self-movement path results in or otherwise contributes to a physical obstacle within the defined printing vicinity, the printing application optionally applies four-dimensional printing capabilities to enable modification of self-movement path shape (e.g., self-movement path condensing and/or folding) in order to reduce the profile of the created self-movement path when not in use.

Figure 7:
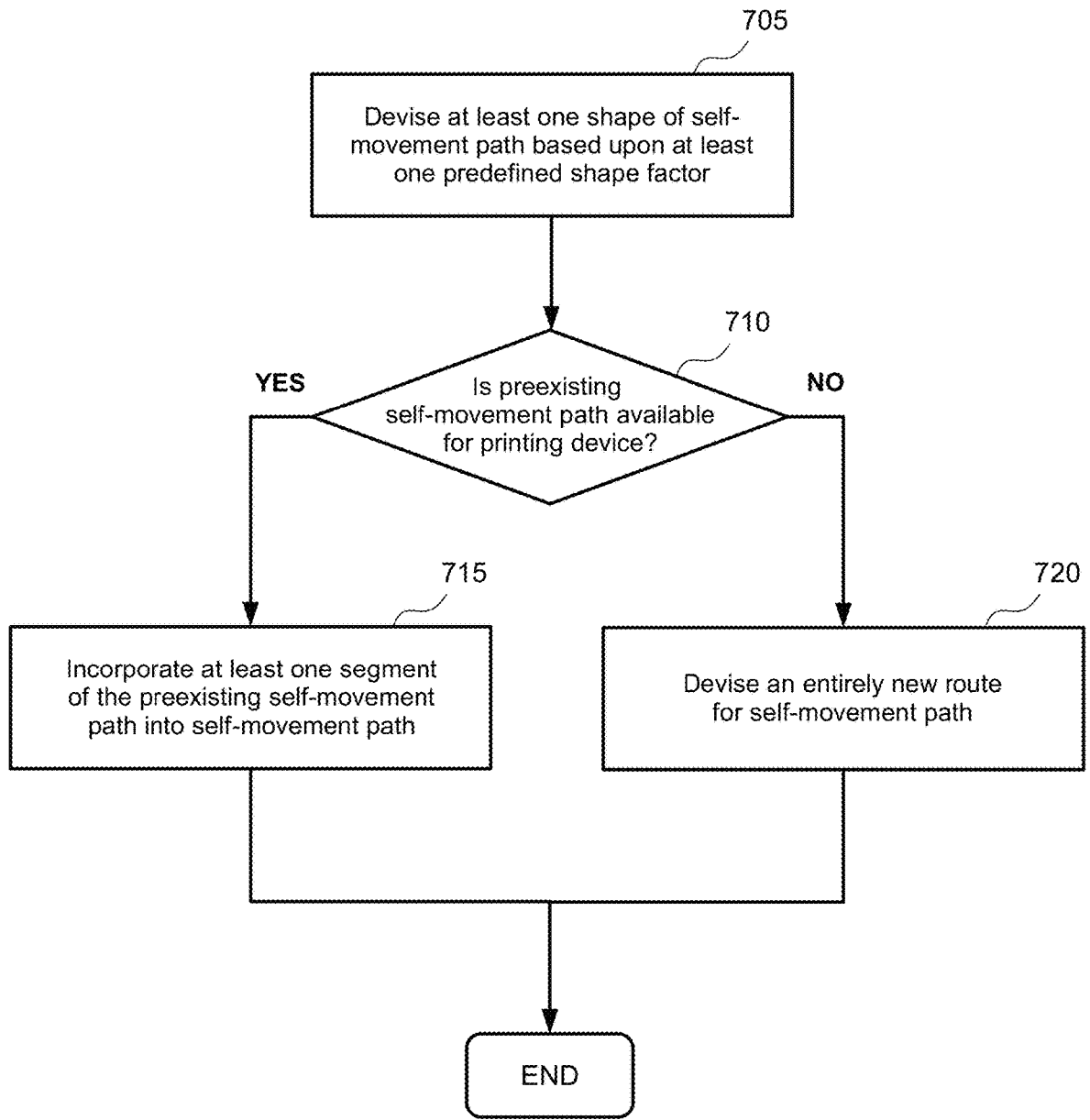
FIG. 7 illustrates a method of facilitating creation of a self-movement path for each of at least one printing device, according to one or more embodiments.

A method with regard to facilitating self-movement path creation for each of the at least one printing device in accordance with step 320 is described herein with respect to FIG. 7. According to a default embodiment, upon creation of the self-movement path for each of the at least one printing device in accordance with step 320, the printing application proceeds to the end of the method 300. According to an alternative embodiment, the printing application optionally returns to step 305 to repeat one or more steps of the method 300, e.g., in the context of a new printing activity.

In an embodiment, the self-movement path created for a certain printing device among the at least one printing device in accordance with step 320 corresponds to a footprint of the processed object. In the context of the various embodiments described herein, a footprint of the processed object is defined as an area, a location, and/or a track within the defined printing vicinity occupied by the object. According to such embodiment, the self-movement path created for the certain printing device is parallel to, coextensive with (i.e., corresponds in extent), and/or has a same length, width, and/or height as, the footprint of the processed object. According to such embodiment, the printing application may determine whether the self-movement path corresponds to the footprint based upon analysis of environmental datapoints among the aggregated environmental datapoints collected from the plurality of environmental sensors within a predefined range of the certain printing device and/or based upon analysis of printing device datapoints among the aggregated printing device datapoints collected from the plurality of printing device sensors associated with the certain printing device. For instance, the printing application may analyze one or more audiovisual datapoints from at least one photographic/video sensor among the plurality of environmental sensors within a predefined range of the certain printing device and/or from at least one photographic/video sensor among the plurality of printing device sensors associated with the certain printing device. In a scenario in which the self-movement path corresponds to the footprint of the processed object, the printing application facilitates creation of the self-movement path and facilitates creation, modification, and/or enhancement of the object simultaneously (i.e., in unison) and/or during a single traversal or single set of traversals within the defined printing vicinity.

Figure 4:
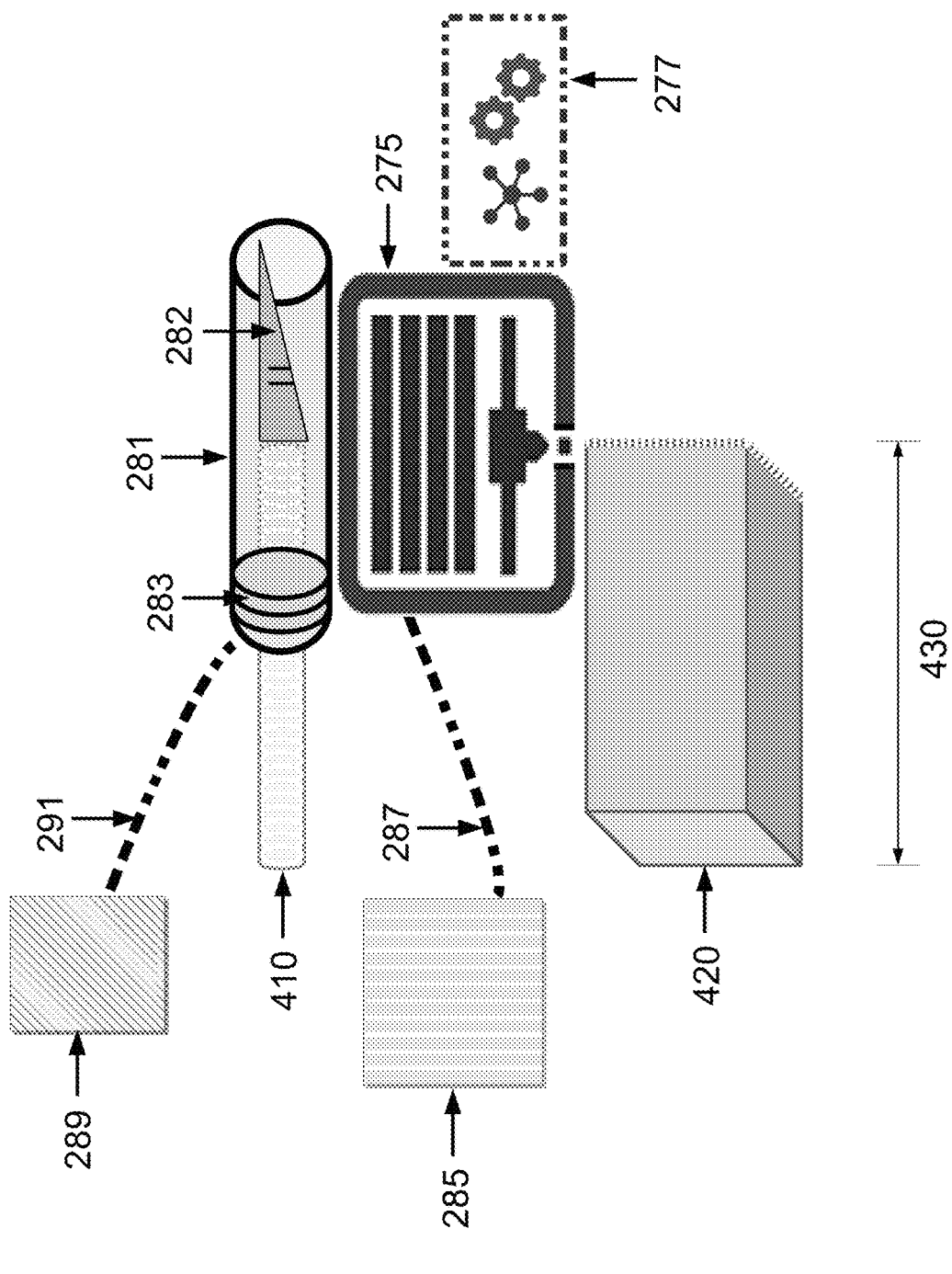
FIG. 4 illustrates a scenario in which a self-movement path created for an example printing device corresponds to a footprint of an object processed in the context of the method illustrated in FIG. 3.

FIG. 4 illustrates an example scenario 400 in which a self-movement path 410 created for example printing device 275 corresponds to a footprint of an object 420 processed in the context of the method 300. Self-movement path 410 optionally is marked or otherwise delineated by a track, e.g., via deposition by dice 281 of printing material stored in one or more of printing material compartments 283. Furthermore, any physical obstruction within self-movement path 410 optionally is reduced or eliminated via at least one blade of cutting element 282. According to scenario 400, printing device creates object 420. As illustrated in FIG. 4, self-movement path 410 is parallel to the footprint of object 420. Furthermore, as indicated by length metric 430, the length of self-movement path 410 corresponds to the length of the footprint of object 420. In the context of another scenario, an analogous metric may account for width or height in lieu of or in addition to length. According to scenario 400, the printing application facilitates creation of self-movement path 410 in accordance with step 320 and further facilitates creation of object 420 simultaneously and/or during a single traversal or a single set of traversals within the defined printing vicinity.

Alternatively, the self-movement path created for a certain printing device among the at least one printing device in accordance with step 320 is separate from a footprint of the processed object. According to such alternative, the printing application facilitates creation of the self-movement path and facilitates processing of the object during separate respective traversals within the defined printing vicinity. Furthermore, according to such alternative, the printing application facilitates creation of the self-movement path prior to facilitating processing of the object (e.g., before object creation or modification) or subsequent to facilitating processing of the object (e.g., after object creation or modification).

Figure 5:
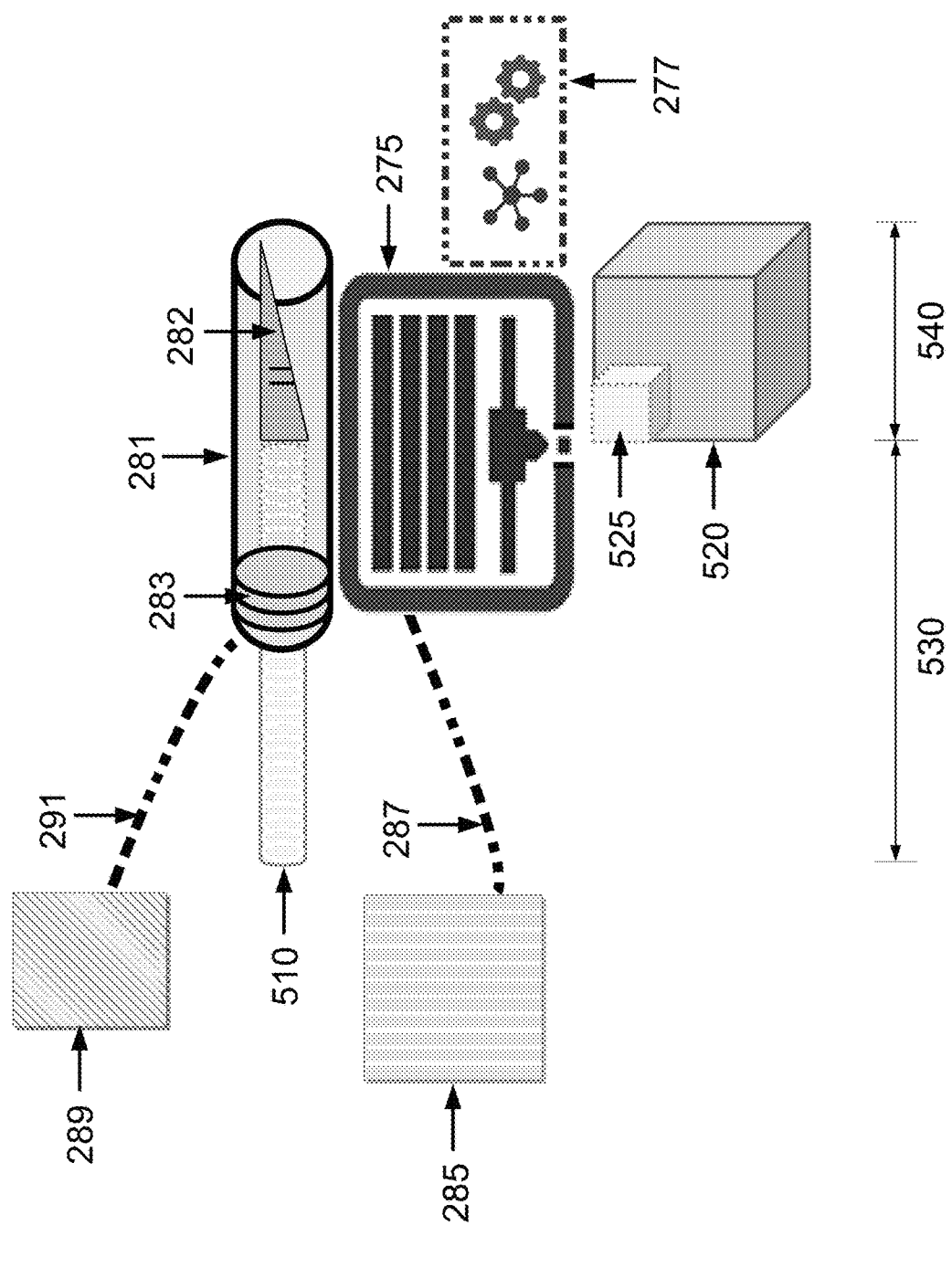
FIG. 5 illustrates a scenario in which a self-movement path created for an example printing device is separate from a footprint of an object processed in the context of the method illustrated in FIG. 3.

FIG. 5 illustrates an example scenario 500 in which a self-movement path 510 created for example printing device 275 in accordance with step 320 is separate from a footprint of an object 520 processed in the context of the method 300. Self-movement path 510 optionally is marked or otherwise delineated by a track. According to scenario 500, printing device 275 modifies portion 525 of object 520. The length of self-movement path 510, as indicated by length metric 530, differs and is separate from the length of the footprint of object 520, as indicated by length metric 540. In the context of another scenario, an analogous metric may account for width or height in lieu of or in addition to length. According to scenario 500, the printing application facilitates creation of the self-movement path and facilitates modification of object 520 during separate respective traversals within the defined printing vicinity. Specifically, the printing application facilitates creation of self-movement path 510 subsequent to creation of the footprint of object 520, i.e., the printing application facilitates creation of the footprint of object 520 initially, and subsequently the printing application facilitates creation of self-movement path 510 in order to modify portion 525 of object 520.

Figure 6:
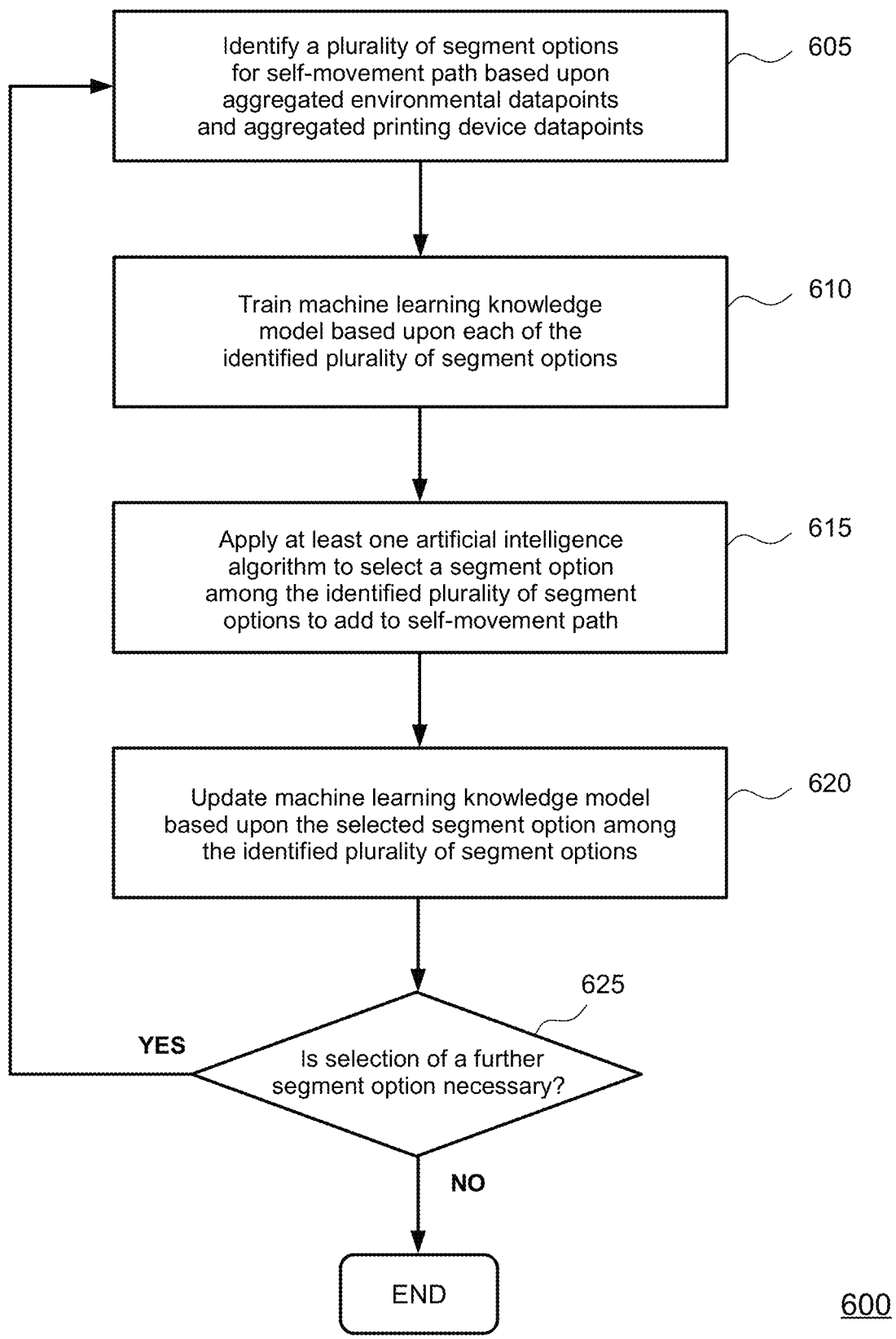
FIG. 6 illustrates a method of configuring a machine learning knowledge model, according to one or more embodiments.

FIG. 6 illustrates a method 600 of configuring the machine learning knowledge model based upon the aggregated environmental datapoints and the aggregated printing device datapoints in order to determine the self-movement path for each of the at least one printing device between the source location associated with the printing device and the target location associated with the printing device. The method 600 provides one or more example embodiments with respect to step 315 of the method 300. In the event that there is a single printing device among the at least one printing device, the printing application executes steps of the method 600 to determine a single self-movement path for the single printing device. Alternatively, in the event that there are multiple printing devices among the at least one printing device, the printing application executes steps of the method 600, optionally multiple times, to determine respective self-movement paths for the multiple printing devices. The method 600 is described in the context of determining the self-movement path for a certain printing device among the at least one printing device; such certain printing device may be a single printing device or among multiple printing devices.

The method 600 begins at step 605, where the printing application identifies a plurality of segment options for the self-movement path based upon the aggregated environmental datapoints and the aggregated printing device datapoints. In an embodiment, the printing application identifies a plurality of segment options between a current location of the printing device and the target location associated with the printing device based upon photographic/video sensor datapoints and/or IoT sensor feed datapoints obtained via at least one photographic/video sensor among the plurality of environmental sensors within a predefined range of the printing device and/or obtained via at least one photographic/video sensor among the plurality of printing device sensors associated with the printing device. Such photographic/video sensor datapoints and/or IoT sensor feed datapoints optionally are associated with camera sensors. At step 610, the printing application trains the machine learning knowledge model based upon each of the identified plurality of segment options. In an embodiment, the printing application trains the machine learning knowledge model in conjunction with a long short-term memory recurrent neural network (LSTM-RNN) architecture configured to store time series pattern data with respect to environmental datapoints, printing device datapoints, and/or segment options. By training the model based upon each of the plurality of identified segment options, the printing application prepares for segment selection and further enhances the model for future iterations.

At step 615, the printing application applies at least one artificial intelligence algorithm (and/or at least one algorithm applicable to the field of artificial intelligence) in order to select a segment option among the identified plurality of segment options to add to the self-movement path. In an embodiment, the aggregated environmental datapoints, the aggregated printing device datapoints, and the plurality of segment options identified at step 605 serve as respective inputs to the at least one artificial intelligence algorithm. According to one embodiment, in order to select a segment option or multiple respective segment options in accordance with step 615, the printing application applies a shortest path algorithm, e.g., Dijkstra's algorithm or Floyd-Warshall algorithm, in order to find a shortest segment from one location to another during determination of the self-movement path. According to a further embodiment, in order to select a segment option or multiple respective segment options in accordance with step 615, the printing application applies a linear regression machine learning algorithm. One such linear regression algorithm optionally is based upon the method of least squares. The method of least squares may address a scenario in which the printing application facilitates determination of self-movement paths for each of multiple printing devices (as opposed to a single self-movement path for a single printing device). Specifically, the printing application applies an algorithm based upon the method of least squares in order to determine selection of segment options that facilitate creation of one or more common path segments incorporated into or otherwise available for multiple self-movement paths for the multiple printing devices. Such one or more common path segments may not necessarily constitute segments of a shortest path between printing device source location(s) and printing device target location(s) but would be optimized in terms of data fitting. Optionally, inputs to the algorithm based upon the method of least squares include aggregated environmental datapoints collected from the plurality of environmental sensors within a predefined range of the multiple printing devices and/or aggregated printing device datapoints collected from the plurality of printing device sensors associated with the multiple printing devices, and outputs to such algorithm include one or more common path segments. Therefore, in the instance of multiple object processing points, e.g., multiple object creation points and/or multiple object modification points, the printing application may apply an algorithm based upon the method of least squares to select self-movement path segment(s) that facilitate mobility and/or guidance of multiple printing devices to multiple object processing points among one or more common path segments. Additionally or alternatively, in the context of the identifying inputs to the algorithm based upon the method of least squares, the printing application optionally receives real time information with respect to movement of one or more of the multiple printing devices along one or more already-created common path segments in order to determine one or more further common path segments. Additionally or alternatively, the multiple printing devices optionally communicate or otherwise collaborate with one another, e.g., via machine to machine communication (M2M communication), in order to pool real time movement information. The printing application optionally receives or otherwise accesses such pooled real time movement information from the multiple printing devices.

In an embodiment, the printing application determines each segment option selected in accordance with step 615 at a defined point in time based upon the aggregated environmental datapoints and the aggregated printing device datapoints identified prior to the defined point in time. According to such embodiment, the printing application dynamically determines successive segments at respective defined points in time consequent to identifying segment options based upon all datapoints aggregated prior and training the machine learning knowledge model based upon the identified segment options. Accordingly, the printing application may identify and select successive segments to add to the self-movement path based upon a cumulative collection of aggregated datapoints that increases as time progress.

At step 620, the printing application updates the machine learning knowledge model based upon the segment option selected among the identified plurality of segment options. Based upon the model update, the printing application may be more capable of selecting at least one further segment option to add to the self-movement path based upon datapoints aggregated with respect to the selected at least one segment option. Based upon the model update, the printing application may be more capable of anticipating (e.g., determining a quantitative probability of) any relevant factor, such as a physical obstruction or another environmental or printing device aspect between a current location of the printing device and the target location associated with the printing device, during selection of one or more further segment options to add to the self-movement path. Additionally or alternatively, based upon the model update, the printing application may be more capable of anticipating (e.g., determining a quantitative probability of) any relevant factor, such as a physical obstruction or another environmental or printing device aspect, during selection of one or more segment options to add to a subsequent self-movement path. For instance, based upon the model update, the printing application may be more capable of determining a quantitative probability of encountering a certain physical obstruction in the context of selecting one or more further segment options to add to the self-movement path and/or in the context of selecting one or more segment options to add to a subsequent self-movement path.

At step 625, the printing application determines whether selection of a further segment option is necessary for purposes of determining the self-movement path between the source location associated with the printing device and the target location associated with the printing device. Responsive to determining that selection of a further segment option is unnecessary for purposes of determining the self-movement path (i.e., segment options have been determined from the source location to the target location), the printing application proceeds to the end of the method 600. Conversely, responsive to determining that selection of a further segment option is necessary for purposes of determining the self-movement path, the printing application returns to step 605, where the printing application identifies a subsequent plurality of segment options for the self-movement path, among which another segment option is selected in accordance with the method 600.

FIG. 7 illustrates a method 700 of facilitating creation of the self-movement path for each of the at least one printing device in order to facilitate object processing within the defined printing vicinity. According to the steps of the method 700, the printing application facilitates creation of the self-movement path for each of the at least one printing device so that each of the at least one printing device may have access to an object for processing, e.g., for creating such object via printing and/or for modifying such object via printing, repairing, and/or otherwise enhancing. The method 700 provides one or more example embodiments with respect to step 320 of the method 300. In the event that there is a single printing device among the at least one printing device, the printing application executes steps of the method 700 to facilitate creation of a single self-movement path for the single printing device. Alternatively, in the event that there are multiple printing devices among the at least one printing device, the printing application executes steps of the method 700, optionally multiple times, to facilitate creation of respective self-movement paths for the multiple printing devices. The method 700 is described in the context of facilitating creation of the self-movement path for a certain printing device among the at least one printing device; such certain printing device may be a single printing device or among multiple printing devices.

The method 700 begins at step 705, where the printing application devises at least one shape of the self-movement path (or one or more respective segments thereof) based upon at least one predefined shape factor. In an embodiment, the printing application selects the at least one predefined shape factor from the group consisting of (i) shape of the processed object, (ii) degree of complexity of the processed object, (iii) available print space, (iv) print frequency, (v) printing device quantity, and (vi) printing device physical attributes, i.e., physical attributes of printing device(s) among the at least one printing device. As for the processed object shape factor, the printing application optionally determines at least one shape of the self-movement path (or one or more respective segments thereof) that aligns with or otherwise corresponds to the shape(s) of the processed object, or the shape(s) of portion(s) thereof. For instance, if the processed object is circular, the printing application may devise a shape of the self-movement path (or one or more respective segments thereof) having one or more circular aspects in order to facilitate appropriate object processing. As for the processed object degree of complexity factor, the printing application optionally determines a level of complexity of the shape of the self-movement path (or one or more respective segments thereof) that aligns with or otherwise corresponds to the level of complexity of the processed object or portion(s) thereof. For instance, the printing application may devise a relatively simple self-movement path shape if the shape of the processed object is simple, while conversely the printing application may devise a relatively complex self-movement path segment shape if the shape of the processed object is relatively complex. In another instance, the printing application may devise a relatively simple self-movement path shape with respect to path segment(s) that correspond to relatively simple portion(s) of the processed object, while conversely the printing application may devise a relatively complex self-movement path shape with respect to path segment(s) that correspond to relatively complex portion(s) of the processed object. As for the available print space factor, the printing application may determine a shape or a combination of shapes that most closely corresponds to the available space for the printing device while providing sufficient physical support for the printing device. As for the print frequency factor, the printing application may determine a relatively sturdier (e.g., thicker and/or more durable) self-movement path shape to address greater print frequency, as greater print frequency may require relatively greater physical support (and thus a studier self-movement path) for the printing device. As for the printing device quantity factor, the printing application may determine a relatively sturdier (e.g., thicker and/or more durable) self-movement path shape responsive to determining a greater quantity of printing devices among the at least one printing device, since in the event that the self-movement path includes one or more common path segments, a greater quantity of printing devices may require relatively greater physical support (and thus a studier self-movement path). As for the printing device physical attributes factor, the printing application may determine at least one shape of the self-movement path that most closely corresponds to a profile of the printing device while providing sufficient physical support for the printing device, in consideration of printing device weight/mass, volume, length, width, height, etc.

In an embodiment, the at least one shape of the self-movement path (or one or more respective segments thereof) as devised by the printing application per step 705 includes spiral elements, e.g., resembling the profile of a spider web. Additionally or alternatively, the at least one shape of the self-movement path (or one or more respective segments thereof) as devised by the printing application includes linear elements, e.g., resembling a profile of a rope or cord. Additionally or alternatively, the at least one shape of the self-movement path (or one or more respective segments thereof) as devised by the printing application includes two-dimensional elements such as circular or polygon-based elements. Additionally or alternatively, the at least one shape of the self-movement path (or one or more respective segments thereof) as devised by the printing application includes three-dimensional elements such as spherical, conical, cylindrical, ellipsoidal, or prism-based elements. In an additional embodiment, the printing application devises distinct shapes for respective segments of the self-movement path. For instance, a self-movement path shape including linear elements may be most appropriate for certain segments of the self-movement path, while a self-movement path shape including cylindrical elements may be most appropriate for other segments of the self-movement path. In a further embodiment, the printing application devises a combination or two or more distinct shapes for the self-movement path or one or more respective segments thereof. For instance, the a self-movement path shape including a combination of linear and cylindrical elements may be most appropriate for the self-movement path or certain segments thereof. In a further embodiment, the printing application analyzes the at least one shape of the self-movement path devised at step 705 by collecting shape-related data from the plurality of environmental sensors and/or the plurality of printing device sensors in order to devise any necessary adjustment to the at least one path shape. According to such further embodiment, upon creation of the self-movement path or at least one segment thereof, the printing application collects sensor data with regard to the physical attributes of the self-movement path or at least one segment thereof (e.g., path length, path width, path height, force(s) applied to the path by printing device(s) or environmental factor(s)) in order to determine whether any path shape adjustment is necessary.

At step 710, the printing application determines whether a preexisting self-movement path between the source location and the target location is available for the printing device. Responsive to determining that a preexisting self-movement path between the source location and the target location is available for the printing device, at step 715 the printing application incorporates at least one segment of the preexisting self-movement path into the self-movement path. In an embodiment, the printing application determines, which, if any, of the at least one segment of the preexisting self-movement path to incorporate based upon any shape constraints as determined per the at least one predefined shape factor in accordance with step 705. In a further embodiment, based upon any shape constraints as determined per the at least one predefined shape factor in accordance with step 705, the printing application may facilitate shape adjustment of one or more of the at least one segment of the preexisting self-movement path upon incorporation into the self-movement path. For instance, if a segment of the preexisting self-movement path to be incorporated does not meet shape constraints as determined in accordance with step 705, the printing application may facilitate adjustment of one or more shape attributes associated with such segment upon incorporation into the self-movement path. Responsive to determining that no preexisting self-movement path between the source location and the target location is available for the printing device, at step 720 the printing application devises an entirely new route for the self-movement path. In an embodiment, the printing application determines at least one segment of the new route based upon any shape constraints as determined per the at least one predefined shape factor in accordance with step 705. In an alternative embodiment, the printing application executes step 705 independently of steps 710-720. In a further alternative embodiment, the printing application executes steps 710-720 independently of step 705.

The descriptions of the various embodiments of the present invention have been presented for purposes of illustration but are not intended to be exhaustive or limited to the embodiments disclosed. All kinds of modifications made to the described embodiments and equivalent arrangements should fall within the protected scope of the invention. Hence, the scope of the invention should be explained most widely according to the claims that follow in connection with the detailed description and should cover all possibly equivalent variations and equivalent arrangements. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method comprising:
   aggregating environmental datapoints related to at least one environmental parameter associated with a defined printing vicinity of at least one printing device;
   aggregating printing device datapoints related to at least one printing hardware parameter associated with the at least one printing device;
   based upon the aggregated environmental datapoints and the aggregated printing device datapoints, configuring a machine learning knowledge model to determine a self-movement path for each of the at least one printing device between a source location of the printing device and a target location of the printing device; and
   facilitating creation of the self-movement path for each of the at least one printing device to facilitate processing of an object within the defined printing vicinity.

2. The computer-implemented method of claim 1, wherein aggregating the environmental datapoints comprises collecting data from a plurality of environmental sensors within the defined printing vicinity.

3. The computer-implemented method of claim 1, wherein aggregating the printing device datapoints comprises collecting data from a plurality of printing device sensors associated with each of the at least one printing device.

4. The computer-implemented method of claim 1, wherein one or more of the at least one printing device include four-dimensional printing capabilities to address or enable self-movement path modification over time.

5. The computer-implemented method of claim 1, wherein the self-movement path created for a certain printing device among the at least one printing device corresponds to a footprint of the processed object.

6. The computer-implemented method of claim 1, wherein the self-movement path created for a certain printing device among at least one printing device is separate from a footprint of the processed object.

7. The computer-implemented method of claim 1, wherein configuring the machine learning knowledge model comprises:
   identifying a plurality of segment options for the self-movement path based upon the aggregated environmental datapoints and the aggregated printing device datapoints; and
   training the machine learning knowledge model based upon each of the identified plurality of segment options; and
   applying at least one artificial intelligence algorithm to select a segment option among the identified plurality of segment options to add to the self-movement path.

8. The computer-implemented method of claim 7, wherein each selected segment option is determined at a defined point in time based upon the aggregated environmental datapoints and the aggregated printing device datapoints identified prior to the defined point in time.

9. The computer-implemented method of claim 7, wherein configuring the machine learning knowledge model further comprises:
   updating the machine learning knowledge model based upon the selected segment option among the identified plurality of segment options.

10. The computer-implemented method of claim 1, wherein facilitating creation of the self-movement path for each of the at least one printing device comprises:
    devising at least one shape of the self-movement path based upon at least one predefined shape factor selected from the group consisting of shape of the processed object, degree of complexity of the processed object, available print space, print frequency, printing device quantity, and printing device physical attributes.

11. The computer-implemented method of claim 1, wherein facilitating creation of the self-movement path for each of the at least one printing device comprises:
    responsive to determining that a preexisting self-movement path between the source location and the target location is available for the printing device, incorporating at least one segment of the preexisting self-movement path into the self-movement path.

12. The computer-implemented method of claim 1, wherein facilitating creation of the self-movement path for each of the at least one printing device comprises:
    responsive to determining that no preexisting self-movement path between the source location and the target location is available for the printing device, devising an entirely new route for the self-movement path.

13. A computer program product comprising a computer readable storage medium having program instructions embodied therewith, the program instructions executable by a computing device to cause the computing device to:
    aggregate environmental datapoints related to at least one environmental parameter associated with a defined printing vicinity of at least one printing device;
    aggregate printing device datapoints related to at least one printing hardware parameter associated with the at least one printing device;
    based upon the aggregated environmental datapoints and the aggregated printing device datapoints, configure a machine learning knowledge model to determine a self-movement path for each of the at least one printing device between a source location of the printing device and a target location of the printing device; and
    facilitate creation of the self-movement path for each of the at least one printing device to facilitate processing of an object within the defined printing vicinity.

14. The computer program product of claim 13, wherein one or more of the at least one printing device include four-dimensional printing capabilities to address or enable self-movement path modification over time.

15. The computer program product of claim 13, wherein configuring the machine learning knowledge model comprises:
    identifying a plurality of segment options for the self-movement path based upon the aggregated environmental datapoints and the aggregated printing device datapoints; and
    training the machine learning knowledge model based upon each of the identified plurality of segment options; and
    applying at least one artificial intelligence algorithm to select a segment option among the identified plurality of segment options to add to the self-movement path.

16. The computer program product of claim 15, wherein configuring the machine learning knowledge model further comprises:
    updating the machine learning knowledge model based upon the selected segment option among the identified plurality of segment options.

17. A system comprising:
    a processor; and
    a memory storing an application program, which, when executed on the processor, performs an operation comprising:
        aggregating environmental datapoints related to at least one environmental parameter associated with a defined printing vicinity of at least one printing device;
        aggregating printing device datapoints related to at least one printing hardware parameter associated with the at least one printing device;
        based upon the aggregated environmental datapoints and the aggregated printing device datapoints, configuring a machine learning knowledge model to determine a self-movement path for each of the at least one printing device between a source location of the printing device and a target location of the printing device; and
        facilitating creation of the self-movement path for each of the at least one printing device to facilitate processing of an object within the defined printing vicinity.

18. The system of claim 17, wherein one or more of the at least one printing device include four-dimensional printing capabilities to address or enable self-movement path modification over time.

19. The system of claim 17, wherein configuring the machine learning knowledge model comprises:
    identifying a plurality of segment options for the self-movement path based upon the aggregated environmental datapoints and the aggregated printing device datapoints; and
    training the machine learning knowledge model based upon each of the identified plurality of segment options; and
    applying at least one artificial intelligence algorithm to select a segment option among the identified plurality of segment options to add to the self-movement path.

20. The system of claim 19, wherein configuring the machine learning knowledge model further comprises:
    updating the machine learning knowledge model based upon the selected segment option among the identified plurality of segment options.

* * * * *